(12) United States Patent
Cheng et al.

(10) Patent No.: US 6,197,920 B1
(45) Date of Patent: Mar. 6, 2001

(54) FORMULATION FOR THE PRODUCTION OF 1, 3-BIS (4-AMINOPHENOXY) NAPHTHALENE AND ITS POLYMER

(75) Inventors: Kun Lin Cheng; Wen-Tung Chen, both of Tu-Cheng (TW)

(73) Assignee: China Textile Institute, Taipei Hsien (TW)

( * ) Notice: Subject to any disclaimer, the term of this patent is extended or adjusted under 35 U.S.C. 154(b) by 0 days.

(21) Appl. No.: 09/357,996

(22) Filed: Jul. 21, 1999

(51) Int. Cl.$^7$ .......................... C08G 73/10; C08G 69/00; C07C 217/90
(52) U.S. Cl. .......................... 528/353; 528/125; 528/128; 528/170; 528/171; 528/172; 528/173; 528/174; 528/176; 528/183; 528/184; 528/185; 528/188; 528/220; 528/229; 528/310; 528/321; 528/322; 528/324; 528/331; 528/332; 528/335; 528/337; 528/350; 528/352; 564/428

(58) Field of Search ...................................... 528/183, 188, 528/324, 220, 229, 176, 331, 185, 184, 332, 125, 350, 352, 128, 171, 321, 170, 335, 172–173, 174, 353, 310, 322, 337; 564/428

(56) References Cited

U.S. PATENT DOCUMENTS 5,340,904 * 8/1994 Yang et al. ........................... 528/353
5,478,913 * 12/1995 Boyce et al. ......................... 528/353
5,886,131 * 3/1999 Yao et al. ............................ 528/185

* cited by examiner

*Primary Examiner*—P. Hampton-Hightower
(74) *Attorney, Agent, or Firm*—Rosenberg, Klein & Lee

(57) ABSTRACT

The present invention relates to the synthesis of new type of diamine monomer, 1,3-bis(4-amonophenoxy)naphthalene, and with such a compound to produce a series of aromatic polymers, including polyamide, polyimide, copoly(amide-imide)s, etc., such polymers having excellent resistance to heat and mechanical properties.

5 Claims, No Drawings

FORMULATION FOR THE PRODUCTION OF 1, 3-BIS (4-AMINOPHENOXY) NAPHTHALENE AND ITS POLYMER

FIELD OF THE INVENTION

The present invention relates to bisphenoxy-containing 1,3-bis (4-aminophenoxy) naphthalene), and thereby of a series of aromatic polymers, including polyamide, polyimide, copoly(amide-imide)s, etc. are produced.

BACKGROUND OF THE INVENTION

Aromatic diamine has been widely used in the fields of high-performance high polymers, such as p-phenylenediamine for the production of Kevlar, m-phenylenediamine for the production of Nomex, and 4,4'-oxydianiline for the production of Kapton; therefore, the potentiality of aromatic diamine has been more and more explored.

At the present, naphthalene-containing diamine, such as 1,5-nathalene diamine, is frequently used for the production of high-performance high polymers, such naphthalene-containing high polymers have better resistance to heat and better frigidity. Structures of naphthalene ether-containing diamines use dihydroxynaphthalene and p-chloronitrobenzene or p-fluoronitrobenzene to produce dinitro compound, before it is reduced to diaminide. Such prior art includes:

(A) U.S. Pat. No. 5,340,904 had disclosed various replacement of synthesis of bis(4-aminophenoxy) naphthalene, with its substituted position subsitution groups in naphthalene ring including (1,4), (1,5), (1,6), (1,7), (2,3), (2,6) and (2,7);

(B) The U.S. Pat. No. 5,076,817 has mentioned the application of bis(4-aminophenoxy)naphthalene of substituted;

(C) Chemical Abstrat: CA)Vol.117: 191511j has mentioned the synthesis of replacement positions of 1,6 of bis(4-aminophenoxy)naphthalene, using 1,6-dihydroxynaphthalene and p-chloronitrobenzene as preliminary ingredients.

(D) Japanese Patent 1989 No. 33166 has mentioned that 2,6-bis(4-aminophenoxy)naphthalene with 2,6 substitutions in order to produce soluble polyimide.

From the above prior art, it is known that there is no literature or report of substituted positions of 1,3 with bis(4-aminophenoxy), or related polymer technolgy. The 1,4-bis(aminophenoxy naththalene can not be produced from p-chloronitrobenzene and 1,4-dihydroxynaphthalene. However with the subject invention of 1,3-bis(4-aminophenoxy)naphthalene, high yield of dinitro compound could easily be produced from the reaction of 1,3-hydroxynaphthalene with p-fluoronitrobenzene or p-fluoronitrobenzene, which is then reduced to diamine compound, so it is a new type of compound.

The present invention synthesizes the new compound of 1,3-bis(4-aminophenoxy)naphthalene, then with this diamine to produce a series of aromatic polyamide, polyimide and various copoly(amideOimide)s, this series of polymers have excellent resistance to heat and good mechanical properties.

The molecular structure of 1,3-bis(4-aminophenoxy) naphthalene is as follows:

(1) diamine:

[1,3-bis(4-aminophenoxy)naphthalene]

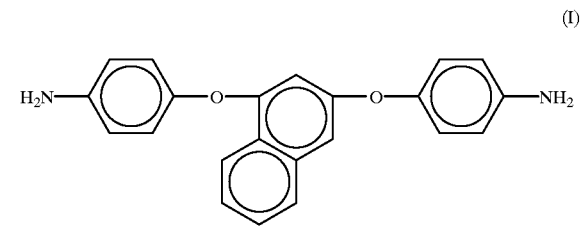

(I)

(2) polyamide:

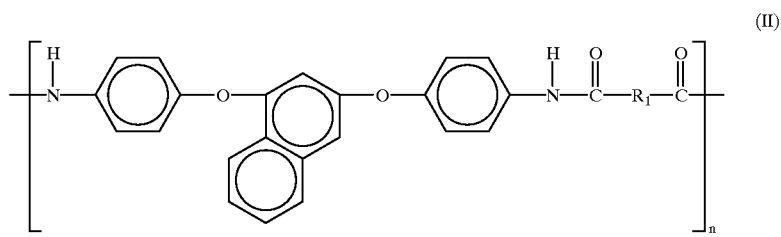

(II)

In structure (II), $R_1$ is

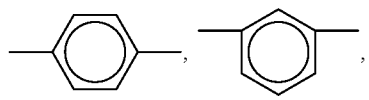

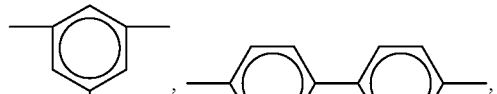

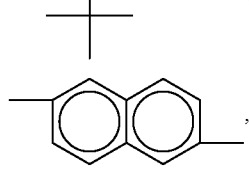

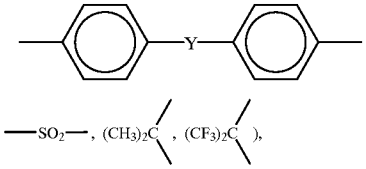

$(Y = -SO_2-, (CH_3)_2C\diagup, (CF_3)_2C\diagup)$, $-(CH_2)_m-$ (m=2—12);

n is an integer between 10–600.

(3) polyimide:
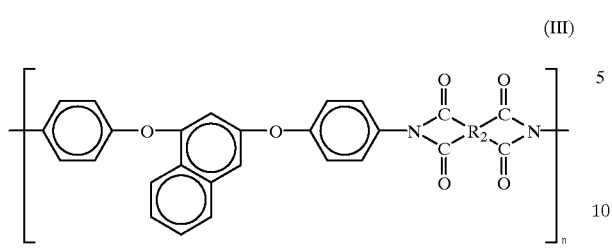
In structure (III), $R_2$ is
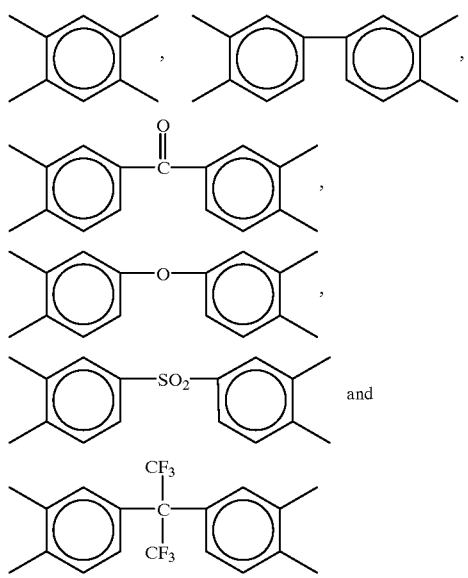
and
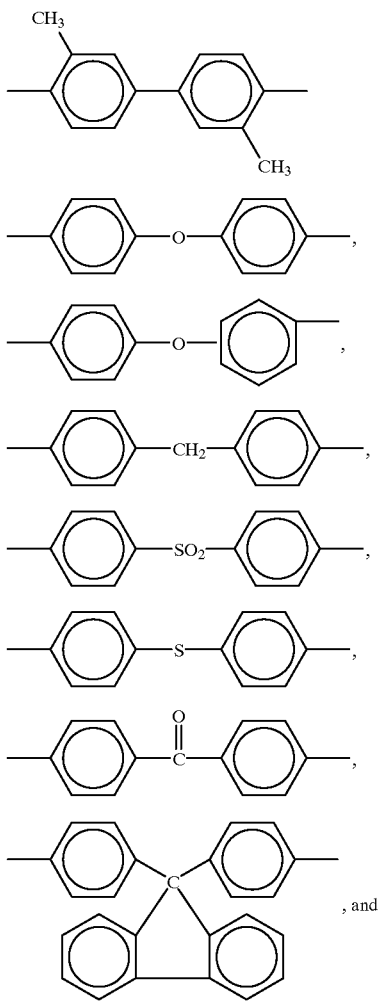
Nn is an integer between 5–600.
(4) polyamide-imide
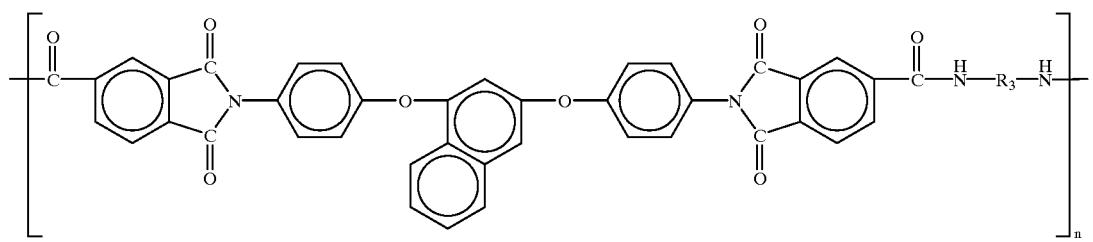
in structure (IV), $R_3$ is
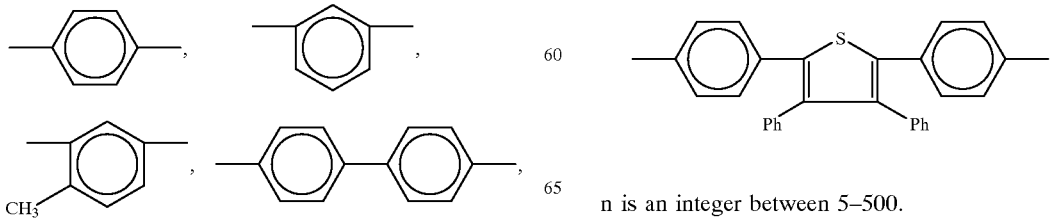
n is an integer between 5–500.
(5) polyamide-imide

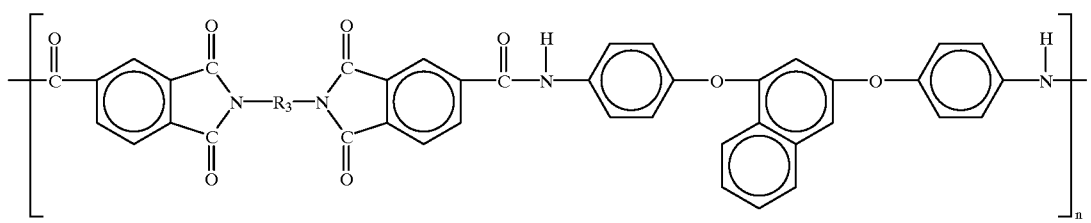

in structure (V), $R_3$ is the same as that shown in the above structure (IV), n is an integer between 10–600.

The preparation for the production of diamine and polymer:

The feature of the present invention is the position of bi-diphenylether group in naphthalene ring (1,3), such diamine has not been disclosed in previous literature, so it is a new compound.

(I) It can be produced from the condensation of 1,3-dihydroxynaphthalene and p-halonitrobenzene, which is then hydrogenated.

Its chemical reaction is shown as follows:

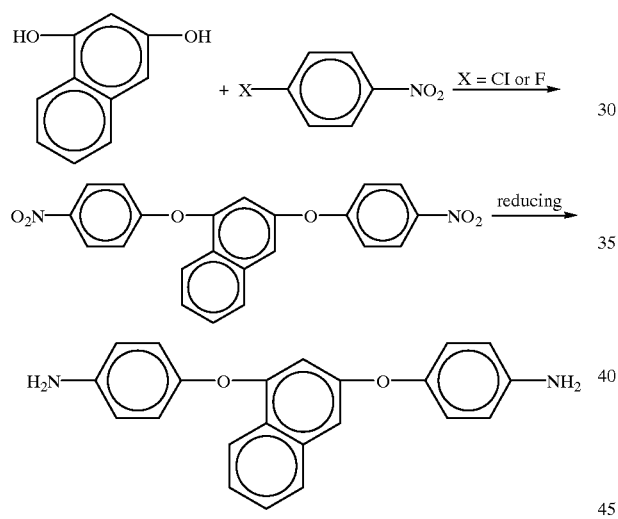

Condensation reaction can be accomplished by heating in an aprotic solvent under alkaline condition. Hydrogenating reaction can be made with metal reducing catalyst (such as palladium catalyst) with the introduction of hydrogen, or hydrazine can be used as the reducing agent to obtain the compound described in (I).

(2) polyamide (II)

Synthesis of polyamide of 4-aminophenoxy naphthalene is made by condensation polymerization of diamine (I) with dicarboxylic acid or activated dicarboxylic acid In direct reaction with dicarboxylic acid, tripheyl phosphite-pyidine can be used as a condensating agent. In the reaction with activated dicarboxylic acid, such as diacid chloride, direct reaction can be made using aprotic solvent such as DMAc (dimethylacetamide) or NMP(N-methglpyrrolidone).

Its reaction formula as follows:

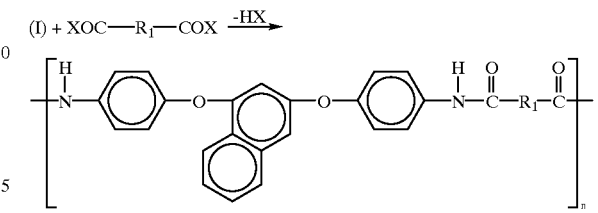

In the formula: x indicates OH or Cl $R_1$ is the same as shown in formula (II)

(3) polyimide (III)

(II) is a series of polyimide containing naphthalene diphenylether group. It is produced by putting diamine (I) with aromatic anhydride in an appropriate organic solvent, which is condensed to have synthetic polyamic acid, then it is heated or added with a dehydrating agent (such as acetic anhydride), to proceed with polymerization condensation to have polyimide, its chemical reaction is shown in the following formula:

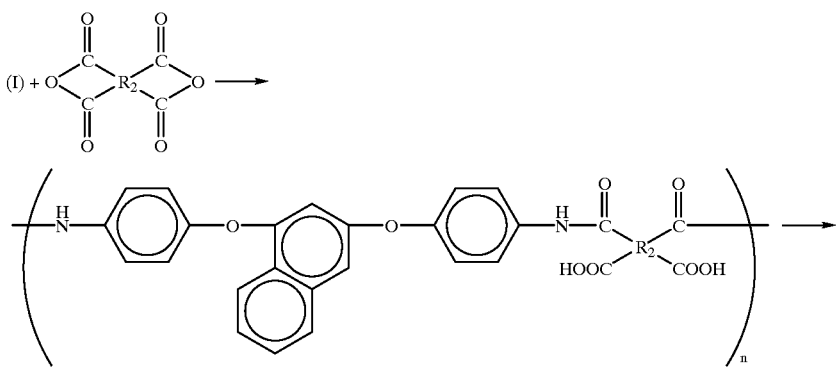

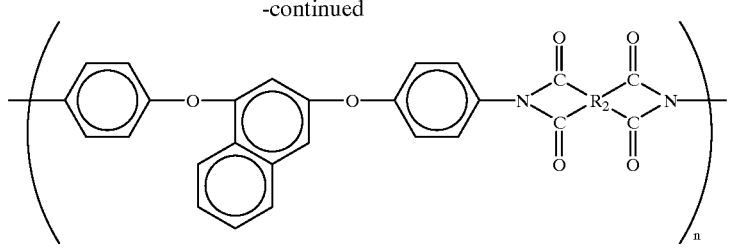

In the formula, $R_2$ is the same as shown in above formula (III).

(4) plymide-polyimide (IV)

((IV) is dicarboxylic acid containing imide, produced by condensation of diamine (I) with Trimellitic Anhydride, which is then polymerized and condensed with a series of diamine.

In mole ratio. 1:2 of the above 1,3-bis(4aminophenoxy) naphthalene, which is heated in an appropriate solvent for dehydration and condensation in order to produce(VI), dicarboxylic acid (VI) is then condensed with a series of diamine. In the polymerization condensation of polymer IV, direct polymerization condensation of triphenyl phosphite/ pyridine is recommended, its reaction formula as follows:

In the formula, $R_3$ is the same as shown in the above formula (IV).

(5) polyamide-polyimide (V)

(V)) is a series of polyamide-polyimide (V) related to Trimellitic Anhydride. Firstly, a series of diamine is condensed with Trimellitic Anhydride to obtain a series of dicarboxylic acid (VII) containing polyimide, diamine (I) is then mixed with dicarboxylic acid (VII) for polymerization condensation reaction to obtain polymer (V), tripheyl phosphite-pyidine is recommended as the condensing agent, its reaction formula is as follows:

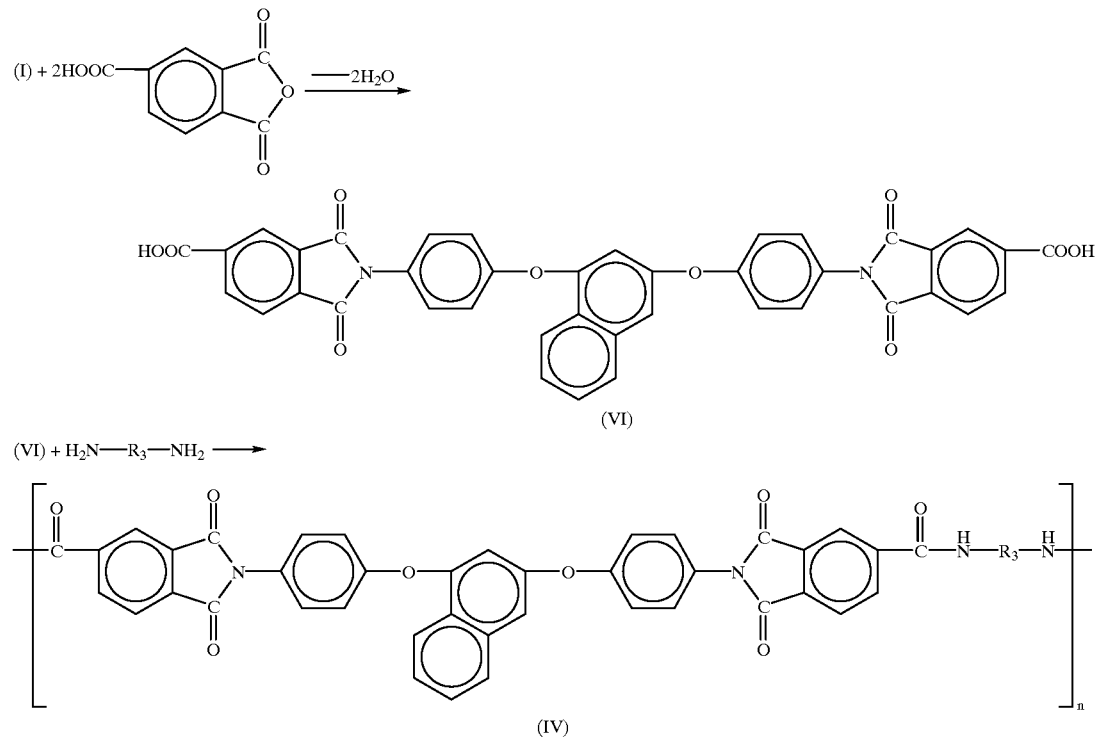

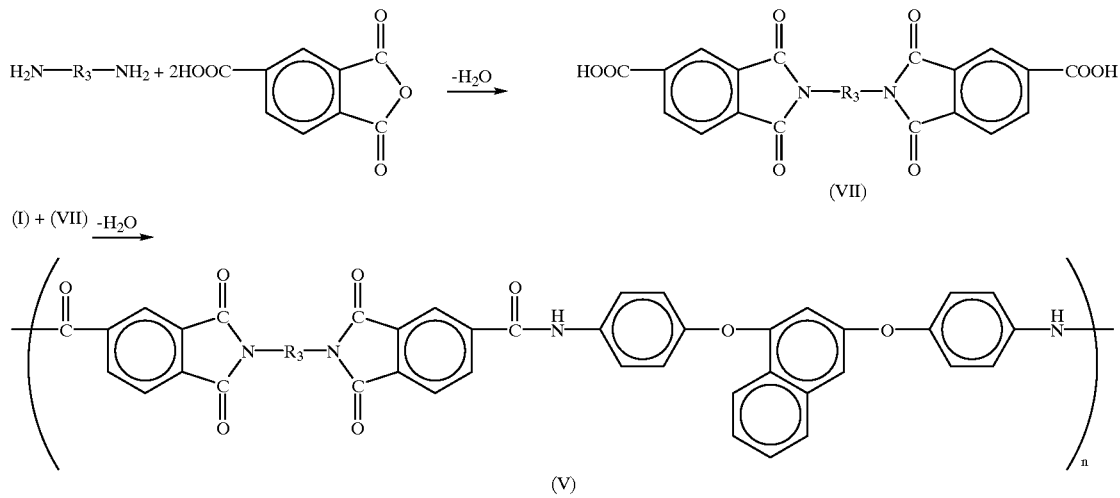

In the formula, $R_3$ is the same as shown in above (IV).

EXAMPLES

Example 1:

Preparation for the production of [1,3-bis(4-aminophenoxy)naphthalene]

In a 500 ml reaction flask, put in 15 grams of 1,3-dihydroxynaphthalene, 26.5 grams of p-fluoronitrobenzene, 27.5 grams of anhydrous potassium carbonate, and 150 ml of N,N-dimethylformamide, mix and flow in cyclone for eight hours at 110° C. After it is cooled, pour in 500 ml of methanol-water mixed liquid (ratio of cubic measurement 1:1), filter the diluted brown powder, cleanse properly with methanol and warm water, then it is dried to obtain 34 grams of dinitro compound (melting point 124~127° C., yield 90%), which is crystallized with glacial acetic acid to obtain yellow crystallized product (melting point at 125° C.

In a 1000 c.c. reaction flask, put in 28 grams of 1,3-bis(4-aminophenoxy)naphthalene, 0.3 grams of Pd/c, and 400 c.c. of ethanol, slowly drip in 60 c.c. of hydrazine at 80° C. After the dripping process, react for further three hours, then filter it when hot, pour the filtered liquid into iced water, to obtain 20 grams of yellow-brown power (yield 84%), melting point at 115° C.

Analysis of elements:

| | | | |
|---|---|---|---|
| Calculation value | C: 77.19% | H: 5.26% | N: 8.18% |
| Analysis value | C: 77.06% | H: 5.56% | N: 8.26% |

Molecular structure

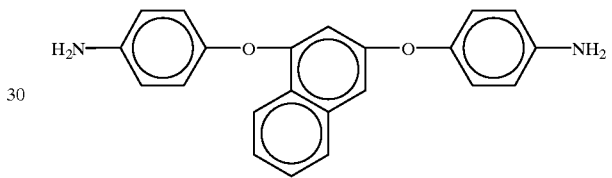

(I)

Example 2:

Preparation for the production of [1,3-bis(4-trimellitimidophenoxy)naphthalene]

In a 100 ml reaction flask, put in 6.8 grams of 1,3-bis(4-aminophenoxy)naphthalene and 8.2 grams of Trimellitic Anhydride, add 30 ml of dehydrated DMF, blend and react to become a transparent solvent, then add 30 ml of methylbenzene, attach Dean-Stark and heat in oil-bath at 140° C., remove water in azeotropic distillation (about 0.72 ml). After the reaction, distill to obtain methylbenzene, after it is cooled, yellow solids will come out slowly, filter it and properly cleanse with methanol, to obtain 13 gams of solids (yield 94%), melting point>350° C.

Analysis of elements:

| | | | |
|---|---|---|---|
| Calculated value | C: 69.56% | H: 3.21% | N: 4.06% |
| Analyzed value | C: 69.41% | H: 3.33% | N: 4.02% |

Molecular structure:

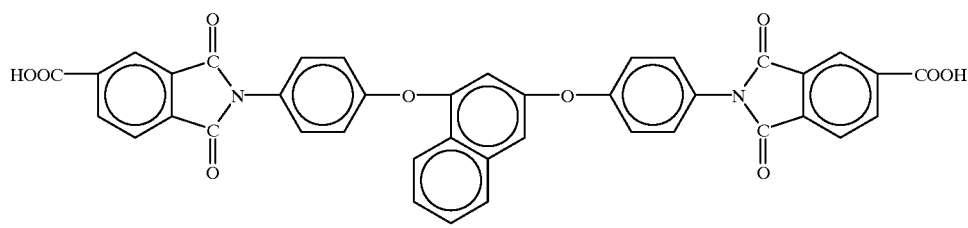

[1,3-bis(4-trimellitimidophenoxy)naphthalene]

Example 3:

Polymide (II)

In a 50 c.c. reaction flask, put in 0.427 grams (1.25 mmole) of 1,3-bis(4-amoniphenoxy)naphthalene, 0.27 grams (1.25 mmole) of 2,6 naphthalene dicarboxylic acid, 0.25 grams of calcium chloride, 4 ml of N-methyl-2-pyrrolidone(NMP), 0.7 c.c. of pyidine and 0.8 c.c. of tripheyl phosphite, then allow reaction for three hours in oil bath at 100° C. to become viscous polymer, pour the reacting liquid in methanol while blending, to obtain silky plymers, which are properly soaked and cleansed in methanol and hot water, then dried to obtain 0.65 grams (99.9%)

Measure inherent viscosity n inh=1.20 dl/g (30° C. in Dimethylacetamide, DMAc). Element analysis value, mechanical strength, resistance to heat and molecular structure as follows:

Element analysis: $(C_{34}H_{22}N_2O_4)n$

| Calculated value | C: 78.19% | H: 4.24% | N: 5.36% |
| Analyzed value | C: 78.11% | H: 4.2% | N: 5.31% |

Mechanical strength:

| yield point strength | Extension rate at break point | starting modulus |
| --- | --- | --- |
| 85 Mpa | 8% | 1.6 Gpa |

10% weight loss temperature:

| in nitrogen | 538° C. |
| in air | 490° C. |

Example 4:

Polyimide (III):

Put in 0.856 grams (2.5 mmole) of 1,3-bis(4-aminophenoxy)naphthalene in 50 ml of reaction flask, add 13.5 c.c of N,N-DMAc to dissolve it, cool with iced water, add several lots of 0.734 grams(2.5 mmole) of 3,3', 4,4'-diphenyl dianhydride, blend with magnet for two hours, measure its inherent viscosity n inh=1.15 dl/g (density 0.5 g/dl in DMAc, 30° C.) of polyamide acid.

Spread a constant thickness of synthesized plyamide acid on a clean cultivating dish, evaporate solvent at 80° C. to become solid films, then increase the temperature in the baking oven, bake for 15 minutes respectively at 110° C., 150° C., 200° C., 230° C. and 250° C., to have yellowish thin films, measure its element analysis value, mechanical strength, resistance to heat and molecular structure as follows:

Element analysis: $(C_{38}H_{20}N_2O_7)n$

| Breaking strength | Extension rate at breaking point | Starting modulus |
| --- | --- | --- |
| 105 Mpa | 12% | 1.80 Gpa |

10% weight loss temperature:

| in nitrogen | 570° C. |
| in air | 563° C. |

Molecular structure

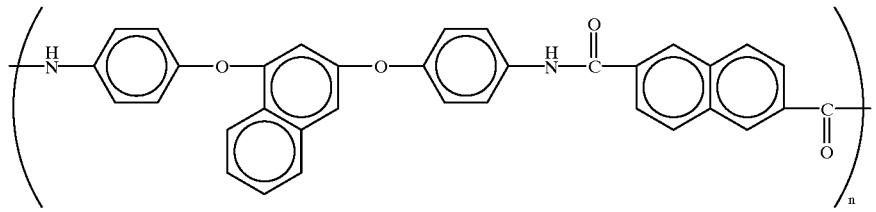

Molecular structure:

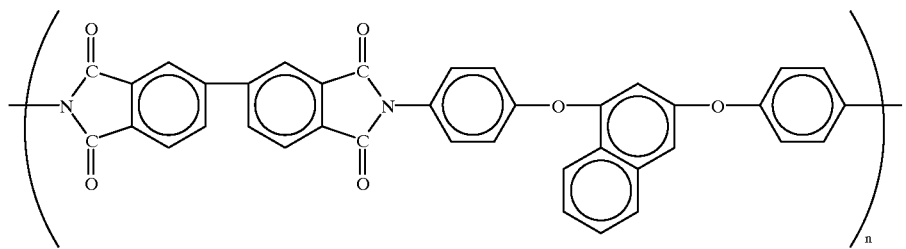

Example 5:

Polyamide-polyimide (IV)

In a 50 c.c. reaction flask, put in 0.86 grams (1.25 mmole) of 1,4-bis(4-trimellitimidophenoxy naphthalene(VI), 0.135 grams (1.25 mmole) of m-phenylenediamine, 8 ml of n-methyl-2-NMP, 0.8 grams of calcium chloride, 1.6 ml of pyidine and 0.8 ml of condensing agent triphel phosphite, allow reaction for three hours at 100° C., pour the viscous substance so formed into methanol while blending, to obtain silky polymers, which is immersed and cleansed properly in methanol and hot water, then dried to obtain 0.953 grams (yield 100%) of polymers, inherent viscosity n inh=1.46 dl/g (0.5 g/dl in DMAc, 30° C.), its element analysis, mechanical strength, resistance to heat and molecular structure as follows:

Element analysis value: $(C_{46}H_{26}N_4O_8)n$

| Calculated value | C: 72.43% | H: 3.43% | N: 7.34% |
| Analyzed value | C: 72.61% | H: 3.52% | N: 7.21% |

Mechanical strength:

| Strength at yield point | Extension rate at breaking point | Starting modulus |
|---|---|---|
| 74 Mpa | 7% | 1.5 Gpa |

10% thermogravimetric loss temperature:

| in nitrogen | 548° C. |
| in air | 526° C. |

Example 6:

Polyamide-polyimide(V):

Take 0.02 mmole of m-phenylenediamine and 0.04 mmole of Trimellitic Anhydride, put them in a 300 ml reaction flask, add 40 ml of anhydrous N,N-dimethyl-DMF, blend to dissolve at 40° C. or lower, then add 20 ml of anhydrous methylbenzene, boil for four hours by azeotropic dehydration, let cool and add methanol to obtain a constant amount of di-imino-dicarboxylic acid:

[1,3-bis(4-trimellitimidophenoxy)naphthalene]

Take out 0.57 grams (1.25 mmole) of dicarboxylic acid imino-dicarboxylic acid and 0.427 grams (1.25 mmole) of 1,3-bis(4-aminophenoxy)naphthalene, in a 50 ml reaction flask, add 0.8 grams of calcium chloride, 8 ml of N-methyl-2-NMP, 1.6 ml of pyidine and 0.8 ml of tripheyl phosphite, blend and allow reaction for three hours at 100° C., pour this viscous liquid into methanol while blending, to obtain silky polymers, which are properly immersed and cleansed in methanol and hot water, and dried to obtain 0.946 grams of polymers (yield 99%), inherent viscosity n inh=0.98 dl/g, the mechanical strength, resistance to heat and molecular structure of DMAc after films are made are as follows:

Mechanical strength:

| Strength at breaking point | Extension rate at breaking point | Starting modulus |
|---|---|---|
| 80 Mpa | 9% | 1.8 Gpa |

10% weight loss temperature:

| in nitrogen | 565° C. |
| in air | 537° C. |

Molecular structure:

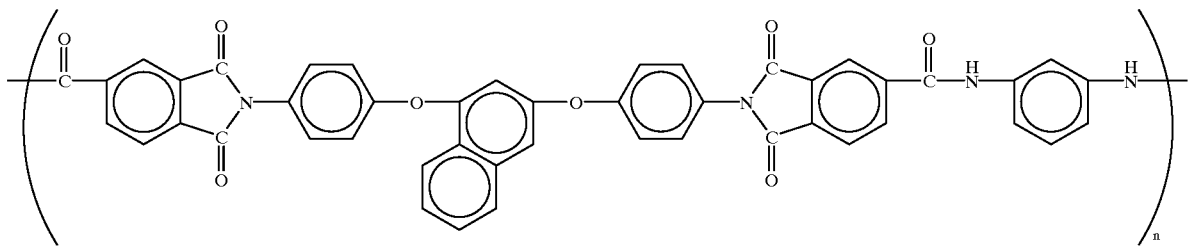

Molecular structure:

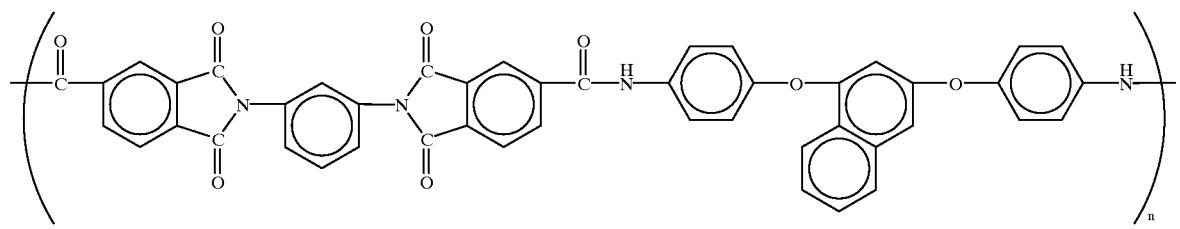

As described above, the subject invention relates to the synthesis of new type of diamine monomer, 1,3-bis(4-aminophenoxy)naphthalene and a series of naphthalene diphenylether group polymers, including polyamide, polyimide, polyamide-polyimide, etc., and such polymers have excellent heat-resistance and mechanical strength for industrial applications.

What is claimed is:

1. A 1,3-bis(4-aminophenoxy)naphthalene, as in the formula (I)

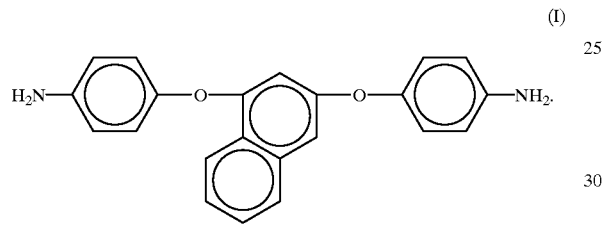

2. A polyamide, as in the formula (II)

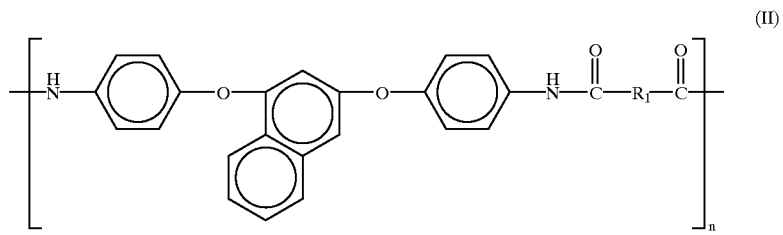

In formula (II), $R_1$ is

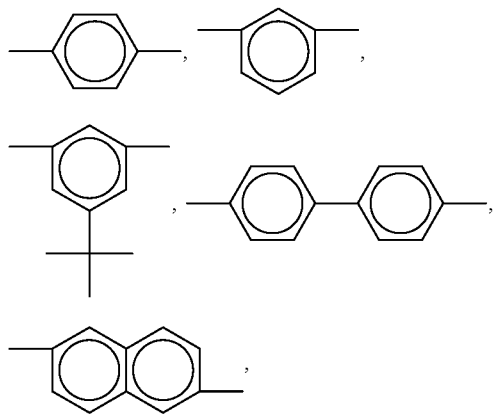

-continued

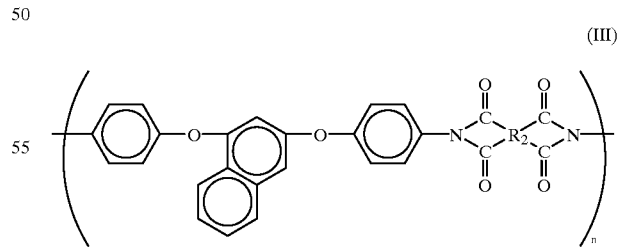

$(Y = -SO_2-, (CH_3)_2C, (CF_3)_2C )$,

While n is an integer between 10–600.

3. A polyimide, as in the formula (III)

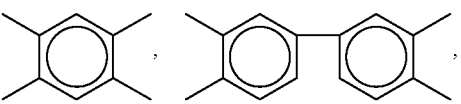

In formula (III), $R_2$ is

-continued
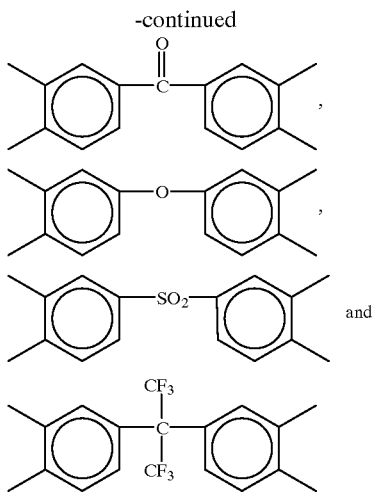
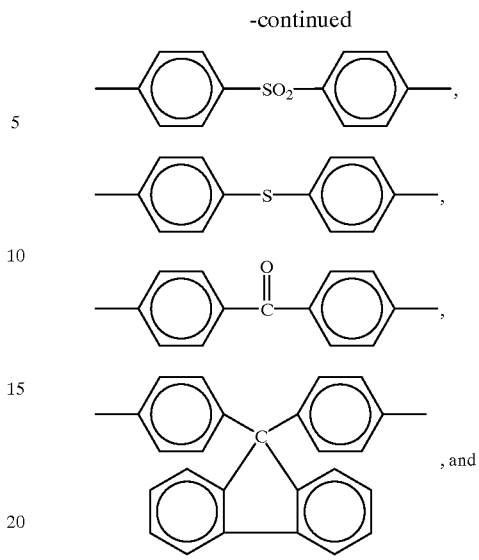
, and
While n is an integer between 5–600.
4. A polyamide-polyimide, as in formula (IV)
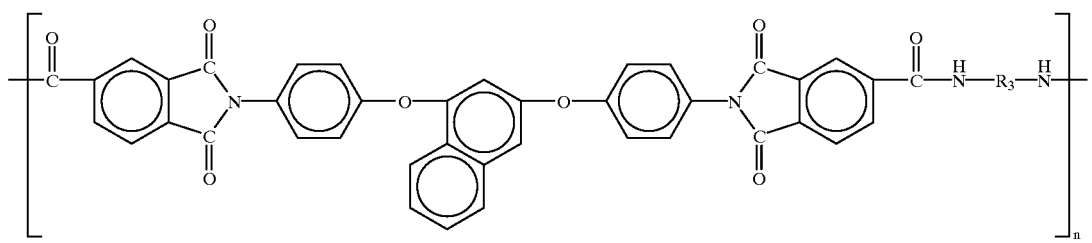
In formula (IV), $R_3$ is
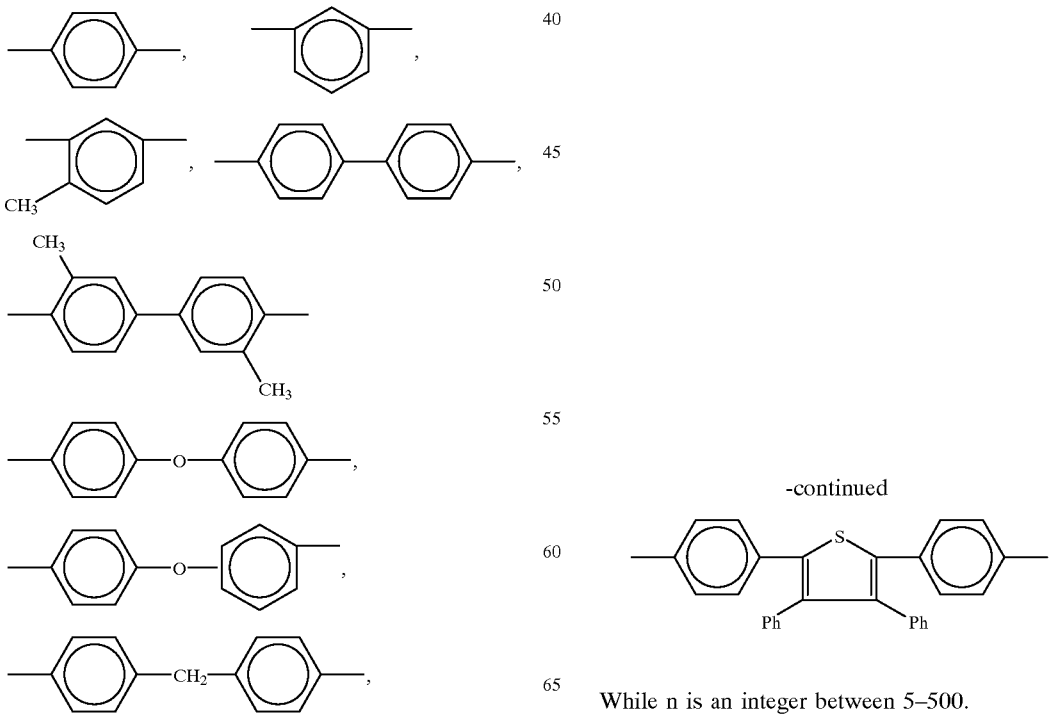
-continued
While n is an integer between 5–500.
5. A polyamide-polyimide, as in formula (V)

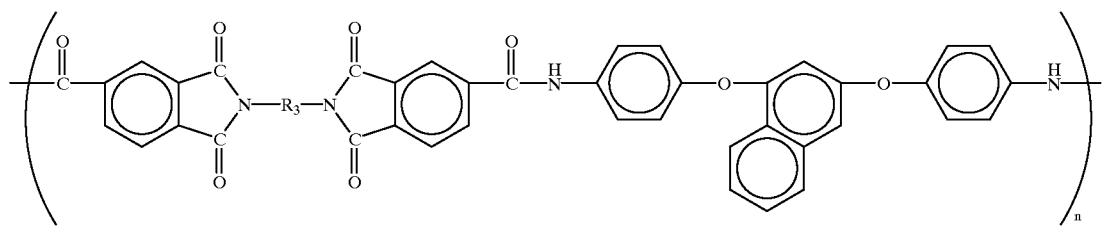
In formula (V), R₃ is
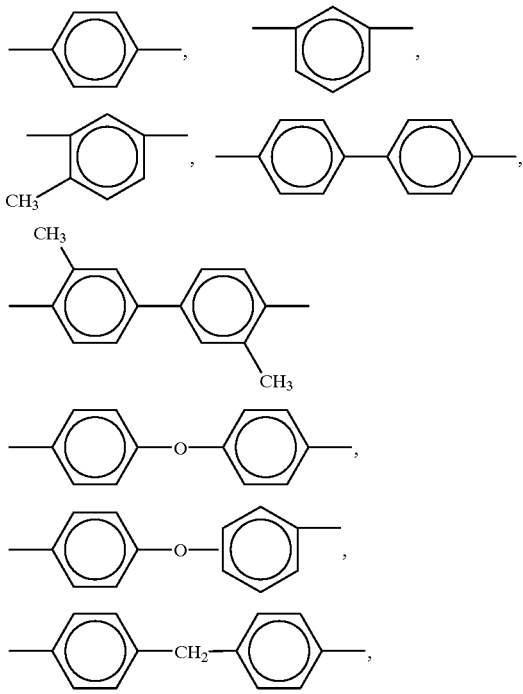
While n is an integer between 10–600.
* * * * *